United States Patent [19]

Wilson

[11] Patent Number: 5,274,088

[45] Date of Patent: Dec. 28, 1993

[54] METHOD FOR THE PREPARATION OF (25R)-26-AMINOCHOLESTEROL

[75] Inventor: Stephen R. Wilson, Chatham, N.J.

[73] Assignee: New York University, New York, N.Y.

[21] Appl. No.: 908,259

[22] Filed: Jul. 2, 1992

[51] Int. Cl.$^5$ .................. C07J 75/00; C07J 43/00
[52] U.S. Cl. ........................... 540/109; 552/544
[58] Field of Search ..................... 552/544; 540/109

[56] References Cited

U.S. PATENT DOCUMENTS

| | | |
|---|---|---|
| 3,156,619 | 11/1964 | Bertin et al. |
| 3,271,250 | 9/1966 | Kanazawa et al. |
| 3,291,690 | 12/1966 | Bertin et al. |
| 3,839,565 | 10/1974 | Saltzman |
| 4,427,668 | 1/1984 | Javitt |
| 4,939,134 | 7/1990 | Javitt et al. |

OTHER DOCUMENTS

*Chemical Abstracts*, Vol. 79, Abstract No. 144832b (1973).
*Chemical Abstracts*, Vol. 82, Abstract No. 13692v (1975).
*Chemical Abstracts*, Vol. 94, Abstract No. 27444a (1981).
*Chemical Abstracts*, Vol. 96, Abstract No. 65246m (1981).
*Chemical Abstracts*, Vol. 98, Abstract No. 103618k (1983).
Uhle et al. (1961) *J. Amer. Chem. Soc.*, Vol. 83, Pages 1460–1472.
Brown et al. "Drugs Used In The Treatment Of Hyperlipoproteinemias," Chapter 34, Pages 827–843, 1986.
G.R. Lenz in "Kirk-Othmer Concise Encyclopedia of Chemical Technology," Wiley Interscience: New York, 1986, Pages 1106–1111.
Varma et al. (1969) *The Journal of Biological Chemistry*, Vol. 244(14), Pages 3951–3957.
Varma et al. (1975) *J. Org. Chem.*, Vol. 40(25), Pages 3680–3686.
Kandutsch et al. (1978) *Science*, Vol. 201(11), Pages 498–501.
Tschesche et al. (1979) *Chem. Ber.*, Vol. 112, Pages 2680–2691.
Arunachalam et al. (1981) *J. Org. Chem.*, Vol. 46, Pages 2966–2968.
Byon et al. (1981) *J. Org. Chem.*, Vol. 46, Pages 3901–3903.
Lin et al. (1981) *J. Steroid Biochem.*, Vol. 14, Pages 563–568.
Teng et al. (1981) *J. Steroid Biochem.*, Vol. 14, Pages 569–573.
G.J. Schroepfer (1981) *Ann. Rev. Biochem*, 50: Pages 585–621.
Javitt et al. (1981) *J. Biol. Chem.*, Vol. 256(24), Pages 12644–12646.
Taylor et al. (1984) *J. Biol. Chem.*, Vol. 259(20), Pages 12382–12387.
White et al. "Hormones and Metabolic Control," D.A. White et al., editors; Edward Arnold Publishers: U.K., 1984, Pages 73–91.
Seo et al. (1986) *J. Chem. Soc. Perkin Trans. I*, Pages 411–414.
Lorenzo et al. (1987) *Federation of European Biochemical Societies*, Vol. 218(1), Pages 77–80.
Miao et al. (1988) *Biochem. J.*, Vol. 255, Pages 1049–1052.
Postlind et al. (1989) *Biochem. Biophys. Res. Comm.*, Vol. 159(3), Pages 1135–1140.
Kudo et al. (1989) *J. Lipid Res.*, Vol. 30, Pages 1097–1111.
Carlson et al. (1989) *Biochem. J.*, Vol. 264, Pages 241–247.
Javitt (1990) *The FASEB Journal*, Vol. 4, Pages 161–168.
Javitt (1990) *J. Lipid Res.*, Vol. 31, Pages 1527–1533.
Rennert et al. (1990) *Endocrinology*, Vol. 127(2), Pages 738–746.
Midland et al. (1985) *Tetrahedron Letters*, Vol. 26(41), Pages 5021–5024.

*Primary Examiner*—Marianne M. Cintins
*Assistant Examiner*—Kimberly J. Kestler
*Attorney, Agent, or Firm*—Darby & Darby

[57] ABSTRACT

This invention relates to a method for the preparation of (25R)-26-aminocholesterol, a potent inhibitor of cholesterol biosynthesis, from (25R)-16-oxo-26-phthalimidocholesterol.

10 Claims, No Drawings

METHOD FOR THE PREPARATION OF (25R)-26-AMINOCHOLESTEROL

FIELD OF THE INVENTION

This invention relates to a method for the preparation of (25R)-26-aminocholesterol, a potent inhibitor of cholesterol biosynthesis.

BACKGROUND OF THE INVENTION

Cholesterol is the major steroid constituent of animal tissue, and is a normal component of plasma and essentially all cell membranes. Cholesterol is a hydrophobic hydrocarbon compound with a reactive hydroxyl group. It is a 3-hydroxy sterol (having a perhydro-1,2-cyclopentenophenanthrene ring system skeleton) with an aliphatic side chain at the C-17 position. In theory, cholesterol plays a major role in regulating the fluidity and permeability of the cell membrane by forming an intercalated structure among the membrane phospholipids.

Cholesterol can be obtained from the diet or synthesized in the liver. It can also be manufactured within the cell, if needed, but in practice most cells receive their cholesterol externally. Cholesterol synthesis occurs according to an enzyme-mediated biosynthetic pathway, in which the rate limiting enzyme is believed to be hydroxymethylglutaryl-Co-A reductase ("HMG CoA reductase") See, for example, Javitt, U.S. Pat. No. 4,427,668. This enzyme catalyzes the formation of mevalonic acid, a cholesterol precursor, from hydroxymethyl glutaric acid. Cholesterol production can be regulated, in theory, by interfering with HMG CoA reductase. Goodman & Gilman, "The Pharmacological Basis of Therapeutics," 7th Ed., MacMillan (New York: 1985), pp. 841-843; Kandustsch et al., Science, 201, 498 (1978).

The excessive accumulation of cholesterol has been implicated as the prime causative factor in a number of diseases. In particular, elevated concentrations of cholesterol can cause and/or hasten atherosclerosis, which is characterized by an abnormal hardening and thickening of the arterial walls due to the accumulation and deposition of fatty materials, including cholesterol. This, in turn, can lead to thrombosis and infarction. For a review of cholesterol-mediated pathologies, see, "Hormones and Metabolic Control," D. A. White, B. Middleton, and M. Baxter, editors; Edward Arnold Publisher; London, 1984, pages 73-90.

The drugs currently in use for the inhibition of cholesterol synthesis have an impact primarily on the liver, and are believed to function by causing upregulation of the LDL receptors of the liver to increase liver uptake of cholesterol and decrease serum levels or by inhibiting HMG CoA reductase, so that cholesterol production is reduced.

Representative of known drugs that are currently in use include mevinolin and cholestyramine, which cause the upregulation of LDL receptors in the liver. Mevinolin, which is an allosteric inhibitor of HMG CoA reductase, achieves this regulation effect by inhibiting cholesterol synthesis in the liver. This stimulates increased LDL receptor activity in the liver, causing hepatic uptake of cholesterol, which in turn reduces plasma cholesterol. Cholestyramine increases the need for bile acid synthesis from cholesterol in the liver, which in some individuals will result in upregulation of LDL receptors. Once again, this reduces plasma cholesterol.

The primary effect of both compounds is therefore limited to the liver. The known compounds are not intended to and do not significantly effect cells outside the liver. A strategy targeted for the liver is effective using the known compounds because, unlike other cells, liver cells can uniquely metabolize (and remove) cholesterol to bile acids. Indeed, compounds such a mevinolin would have a detrimental effect on the accumulation of tissue cholesterol if targeted on cells outside the liver, since the compound would upregulate the LDL receptors and would cause rather than reduce cholesterol accumulation.

Another known compound is 26-hydroxycholesterol which is the subject of U.S. Pat. No. 4,427,668, the disclosure of which is hereby incorporated by reference. See, also Javitt et al., (1981) J.Biol.Chem, Vol. 256(24), pages 12644-12646; Brooks et al., (1983) Biochem Soc. Trans., Vol. 11, pages 700-701; Koopman et al., (1987) J. Chromatogr., Vol. 416, pages 1-13; Esterman et al., (1983) J. Lipid Res., Vol. 24, pages 1304-1309; and Taylor et al., (1984) J. Biol. Chem., Vol. 259(20), pages 12382-12387.

26-hydroxycholesterol is a bile acid intermediate and is believed to have a role in modulating cellular cholesterol homeostasis. For a review of the biological effects of 26 -hydroxy-cholesterol, see, Javitt, N. B. (1990) J. Lipid Res., Vol. 31, pages 1527-1533. Synthetic methods for preparing 26-hydroxy-cholesterol have been reported in the literature. See, for examples, Tschesche et al. (1979) Chem Ber., Vol. 112, pages 2680-2691 and Seo et al. (1986) J. Chem. Soc. Perkin Trans. I, pages 411-416. The described methods generally involve harsh multi-step reactions and produce low yields of the hydroxysteroid.

26-Aminocholesterol was described to be a potent downregulator of LDL receptor and inhibitor of cholesterol biosynthesis in vitro, having equal or greater biological potency than the hydroxyl intermediate. See, Miao et al. (1988) Biochem. J., Vol. 255, pages 1049-1052 and U.S. Pat. No. 4,939,134 (the '134 patent), the disclosures of which are hereby incorporated by reference. This compound is known to selectively inhibit and reduce LDL binding in human fibroblast cells, while having little or no effect on human hepatoma (HepG2) cells. In addition, the compound was also found to downregulate cholesterol synthesis by non-hepatic cells.

Synthetic methods for preparing (25R)-26-aminocholesterol have been reported. Miao et al. (1988) and the '134 patent, for example, describe the preparation of 26-aminocholesterol by a lithium aluminum hydride reduction of 26-azidocholesterol 3-acetate. Tschesche et al. (1979) Chem. Ber., Vol. 112, pages 2680-2691, describes preparation of 26-phthalimidocholesterol and its basic hydrolytic conversion to (25R)-26-aminocholesterol. Preparation of the aminosteroid by these methods, however, requires 26-hydroxycholesterol as starting material, uses complicated protection/deprotection reactions, and results in low yields of the desired product.

Klimova et al., (1982) Khim. Pharm. Zh., Vol. 16, page 451, describes preparation of 26-acetylamino analogs of cholesterol from solasodine, a plant alkaloid and amino analog of diosgenin. According to the described procedure, 3β-acetoxy-26-acetylamino-16,22-dione, derived from oxidation of O,N-diacetylated solasodine, is subjected to a Clemmenson reduction using activated zinc amalgam which produces a mixture of the diacetylated derivatives of 26-aminocholest-5-ene-22-one as a major product and 26-aminocholesterol as a by-product. Because 26-aminocholesterol is produced in low yields, the disclosed reaction is not useful in preparing this aminosteroid. Until now, a simple method for preparing 26-aminocholesterol in high yields has not been available.

It has now unexpectedly been discovered that (25R)-26-aminocholesterol can be prepared directly from simple intermediates, in high yields, and which avoids the need of 26-hydroxycholesterol as starting material and the use of protective group chemistry.

SUMMARY OF THE INVENTION

The present invention provides a method for preparing (25R)-26-aminocholesterol (1) directly from (25R)-16-oxo-26-phthalimidocholesterol (5), by a hydrazine reduction reaction e.g. Wolff-Kishner reaction. The hydrazine reduction reaction simultaneously reduces the 16-oxo moiety and cleaves the phthalimido group. Schemes 1 and 2 illustrate the present method for preparing (25R)-26-aminocholesterol (1) from (25R)-16-oxo-26-phthalimidocholesterol (5).

According to Scheme 1, (25R)-16β-26-dihydroxycholesterol (2), prepared in one step from diosgenin, is selectively reacted at the C-26 hydroxyl group with p-toluene sulfonyl chloride to yield (25R)-16β-26-dihydroxycholesterol 26-tosylate (3) which is then reacted with potassium phthalimide. The resulting (25R)-16β-hydroxy-26-phthalimidocholesterol (4) is then subjected to a modified Jones oxidation which selectively oxidizes the 16β hydroxy group to form (25R)-16-oxo-26-phthalimidocholesterol (5).

Alternatively, (25R)-16β-26-dihydroxycholesterol (2) can be converted, with excess p-toluene sulfonyl chloride, to (25R)-16β-26-dihydroxycholesterol 3,26-ditosylate (6). The ditosylate derivative (6) is then subjected to a modified Jones oxidation to produce (25R)-26-hydroxy-16-oxocholesterol-3,26-ditosylate (7). Compound (7) is then treated with aqueous acidic acetone which selectively hydrolyzes off the C-3 tosyl group and produces (25R)-26-hydroxy-16-oxocholesterol 26-tosylate (8). The C-26 tosylate of compound (8) is then displaced with potassium phthalimide to produce key intermediate compound (5) as described above.

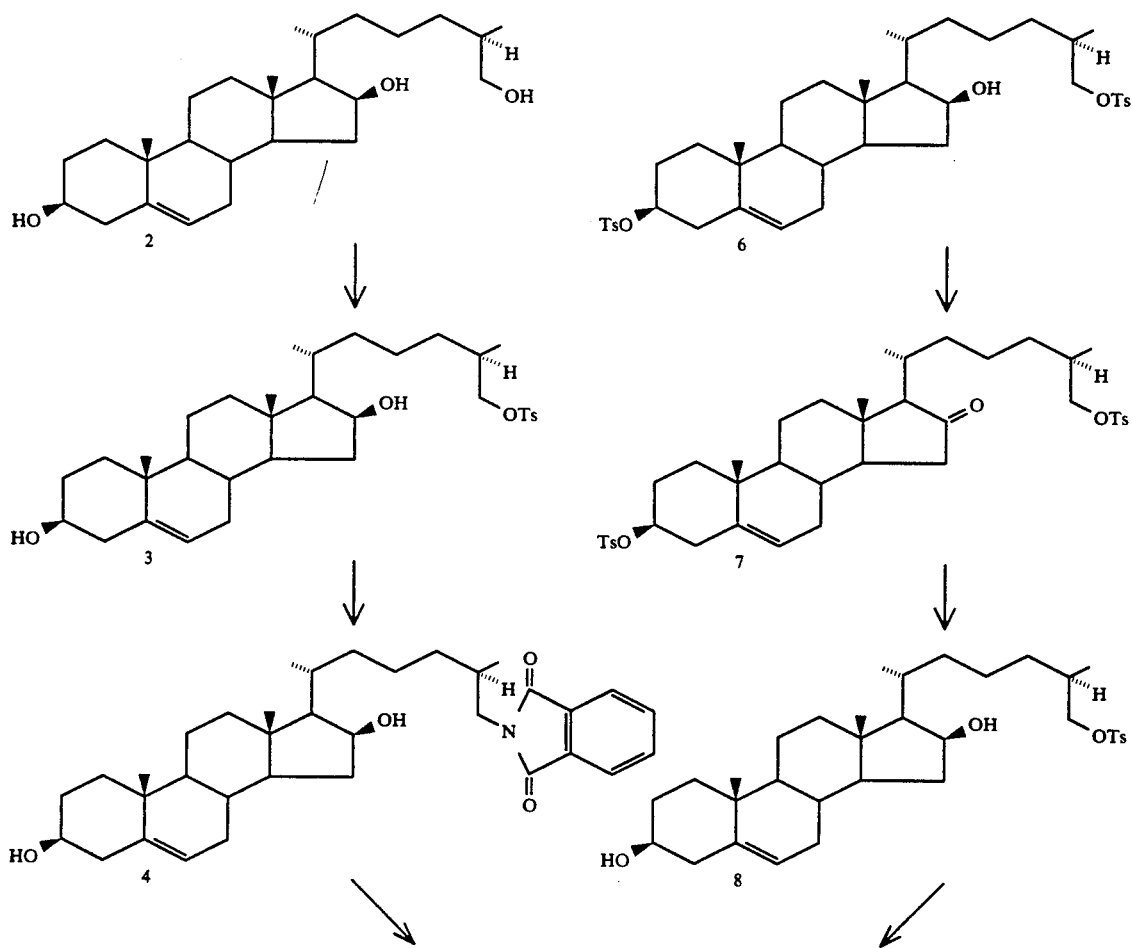

Scheme 1

-continued
Scheme 1

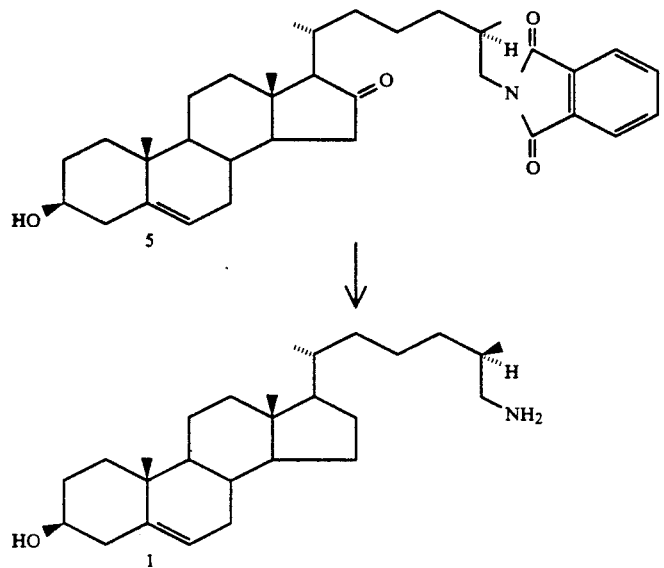

According to Scheme 2, (25R)-16β-26-dihydroxycholesterol (2) is selectively oxidized at the C-16 position to produce (25R)-16-oxo-26-hydroxycholesterol (9). Compound (9) is then converted to the monotosylate (25R)-16-oxo-26-hydroxycholesterol 26-tosylate (8) directly or by indirect means by solvolysis of (25R)-16-oxo-26-hydroxycholesterol 3β,26-diotsylate (7) derived from Compound 9. The C-26 tosylate of compound (8) is then displaced with potassium phthalimide to produce key compound (5) as described above.

Scheme 2

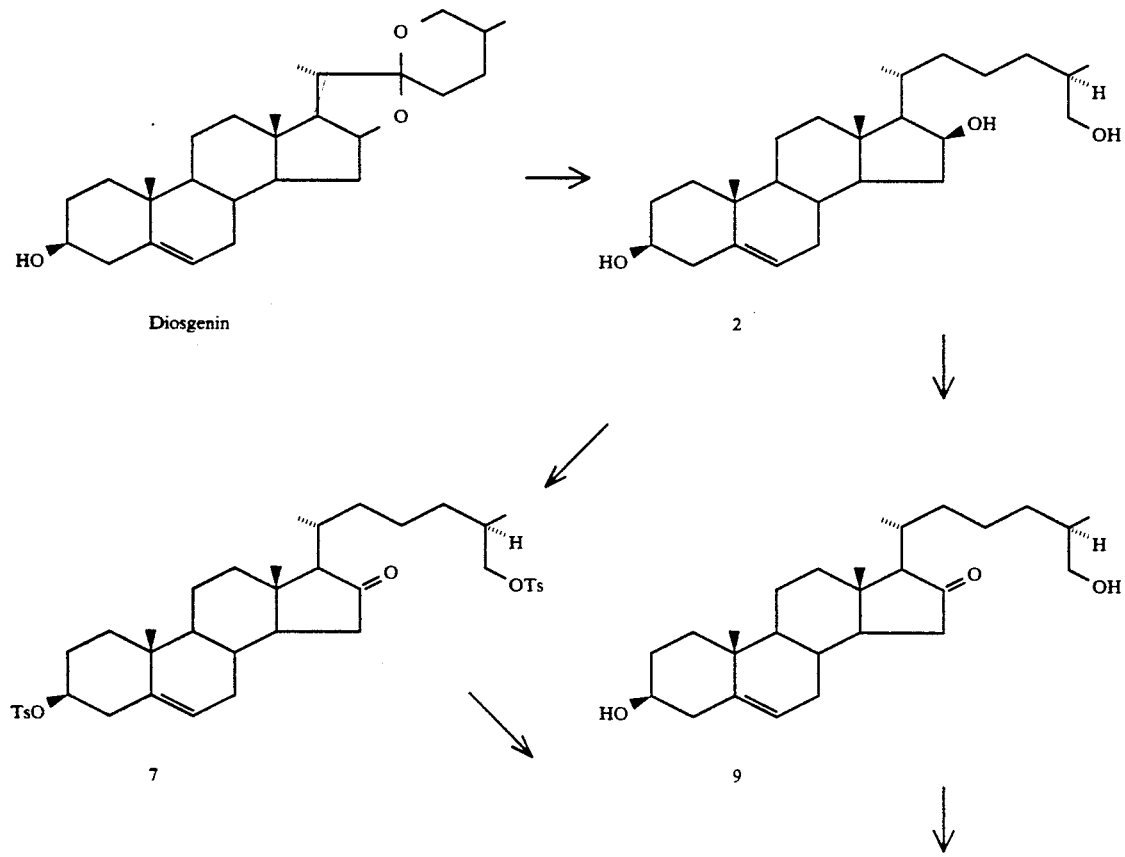

-continued
Scheme 2

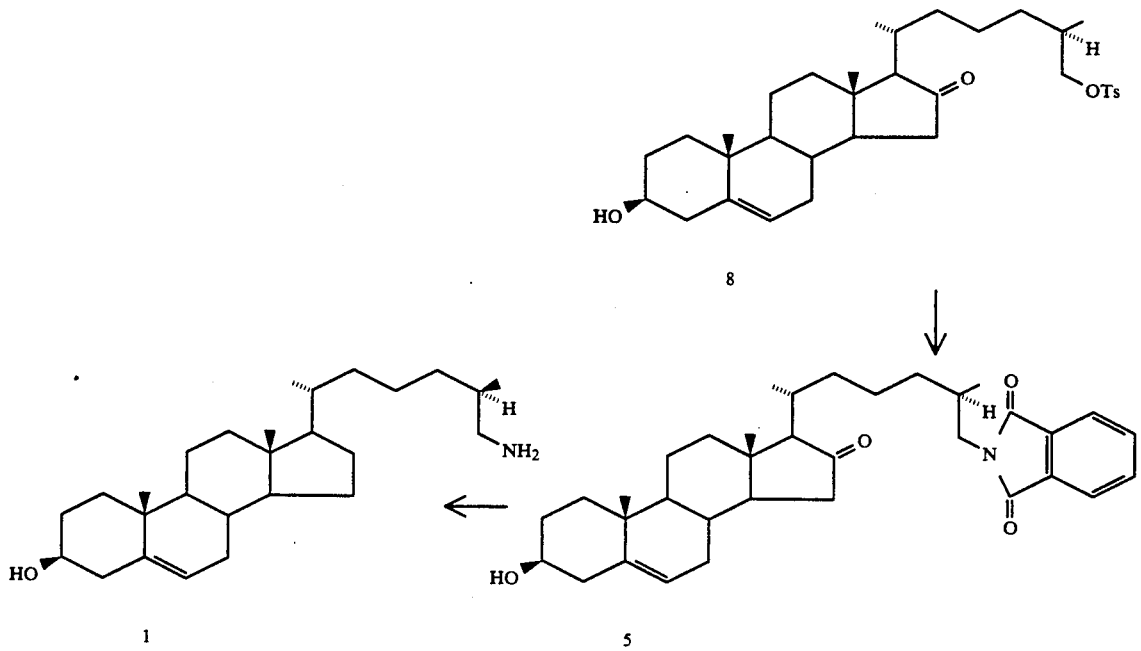

OBJECTS OF THE INVENTION

Accordingly, it is an object of the present invention to provide a simple method for preparing 26-aminocholesterol.

Another object of the present invention is to provide a method for preparing 26-aminocholesterol which avoids the need for 26-hydroxycholesterol as an intermediate and the use of protective group chemistry.

A further object of the invention is to provide a simple and direct method for preparing 26-aminocholesterol in high yields and from readily accessible key intermediate (25R)-16-oxo-26-phthalimidocholesterol (5).

These and other objects of the invention will become apparent in view of the detailed description below.

DETAILED DESCRIPTION OF THE INVENTION

All patents and literature references cited in this specification are hereby incorporated by reference in their entirety.

Chemical reagents and solvents referred to herein are commercially available from Aldrich Chemicals (Milwaukee, Wis., USA), Sigma Co. (St. Louis, Mo., USA), Steraloids (Wilton, N.H., USA), Research Plus (Bayonne, N.J., USA) or Fischer Scientific (Pittsburgh, Pa., USA). All reactions are conducted under an inert atmosphere of nitrogen or argon gas.

According to the method of the present invention, (25R)-16β, 26-dihydroxycholesterol (2) is used as the starting material for preparing (25R)-16-oxo-26-phthalimidocholesterol (5). (25R)-16β, 26-dihydroxycholesterol is prepared from diosgenin, a plant steroid which is commercially available from Sigma Co. or Steraloids. A variety of methods for preparing this intermediate have been described in the literature. See, for example, Tschesche et al. (1979) *Chem. Ber.*, Vol. 112, pages 2680–2691; Arunachalam et al. (1981) *J. Org. Chem.*, Vol. 46, pages 2966–2968; Seo et al. (1986) *J. Chem. Soc. Perkin Trans. I*, Pages 411–414; and Javitt et al. (1990) and references cited in these papers. A particularly preferred method for preparing intermediate (2) can be found in Example 1, which employs unactivated zinc powder in a Clemmenson reduction.

The Clemmensen reduction is an well-known reaction and is typically used for the reduction of carbonyl functionalities and reductive cleavage of acetal groups in organic compounds. For example, the Clemmenson reduction has been used for the reduction of aldehydes and cyclic or acyclic ketones into methylene or methyl groups, respectively, and the reductive cleavage of cyclic steroid acetals such as diosgenin. For a review of this reaction and its proposed mechanism, see, for example, E. Vedejs in "Organic Reactions", John Wiley Publishers, NY, 1975, page 401.

In conducting this reaction, activated zinc metal, in comminuted form such as powder or particles, is required. Methods for producing activated zinc metal (or zinc amalgam) include chemical reduction with mercuric salts, e.g. mercuric chloride, in acidic solution.

It has now been found that when zinc powder, in unactivated for, is used in a Clemmenson reduction of diosgenin, (25R)-16β, 26-dihydroxycholesterol (2) is obtained in surprisingly high yields (>90%) which has not been achieved in reported methods, which utilize zinc amalgam, for making this intermediate.

In practicing this invention, zinc metal powder having a −325 mesh size and a particle size broadly between about 3 microns and about 7 microns, preferably about 4 microns, is useful in the preparation of (25R)-16β, 26--dihydroxycholesterol (2) from diosgenin. A particularly preferred zinc powder for use in this reaction can be obtained from Aldrich Chemical company (St. Louis, Mo., USA).

The amount of zinc metal powder generally ranges between about 50 moles and about 150 moles, preferably about 138 moles, per mole of diosgenin.

According to the synthetic scheme shown in Scheme 1, (25R)-16β, 26-dihydroxycholesterol (2) can be selectively tosylated at the C-26 position to produce intermediate (3) by employing between about 1 and about 2 mole equivalents, preferably between about 1.2 and 1.5 moles, of p-toluenesulfonyl chloride per mole of intermediate (2).

In conducting the tosylation reaction, p-toluene sulfonyl chloride is added to a solution containing (25R)-16β, 26-dihydroxycholesterol (2). Suitable, but non-limiting, solvents useful in conducting this reaction include pyridine or pyridine with $CH_2Cl_2$ as co-solvent. A preferred solvent for use in this invention is pyridine.

The reaction is carried out at a temperature ranging between about 0° C. and about 25° C., preferably about 0° C. for a period ranging between about 10 hours and about 48 hours, preferably about 48 hours. Thereafter, the reaction mixture is poured into water and the monotosylated product, (25R)-16β, 26-dihydroxycholesterol 26-tosylate (3), is extracted from the mixture with an appropriate solvent, e.g. diethyl ether, ethyl acetate, or methylene chloride, and purified by conventional means. Non-limiting purification methods include column or thin layer chromatography and recrystallization. A preferred method of purification is recrystallization from methanol.

Thereafter, (25R)-16β, 26-dihydroxycholesterol 26-tosylate (3) is reacted with a phthalimide salt to form the displacement product, (25R)-16β-hydroxy-26-phthalimidocholesterol (4). Suitable phthalimide salts include sodium or potassium phthalimide. The preferred salt for use in the invention is potassium phthalimide because of its commercial availability.

In conducting the displacement reaction, the phthalimide salt is mixed with a solution containing (25R)-16β, 26-dihydroxycholesterol 26-tosylate (3). Suitable, but non-limiting, solvents useful in conducting this reaction include N,N-dimethylformamide, dioxane, dimethyl sulfoxide. A preferred solvent for use in this invention is N,N-dimethylformamide (DMF).

The reaction is conducted at a temperature ranging between about 25° C. and about 100° C., preferably about 40° C., for a period ranging between about 2 and about 8 hours, preferably about 3 hours.

Thereafter, the reaction mixture is poured into water and the product, (25R)-16β-hydroxy-26-phthalimidocholesterol (4), is extracted from the mixture with an appropriate solvent, e.g. methylene chloride, ethyl acetate, or preferably chloroform, and purified by conventional means, e.g. thin layer or column chromatography and recrystallization. A preferred method of purification is recrystallization from ethyl acetate.

(25R)-16β-Hydroxy-26--phthalimidocholesterol (4) is then selectively oxidized at the C-16 position to form (25R)-16-oxo-26-phthalimidocholesterol (5) with a suitable oxidization system. A particularly preferred system for use in the invention is a glacial acetic acid solution containing chromium trioxide and sodium acetate.

In conducting the oxidation reaction, (25R)-16β-hydroxy-26--phthalimidocholesterol (4) is mixed with a glacial acetic acid solution containing chromium trioxide in an amount between about 1.0 and about 2.0 molar equivalents, preferably about 1.5 molar equivalents, and sodium acetate in an amount between about 20 and about 30 molar equivalents, preferably about 25 molar equivalents per liter of glacial acetic acid. It will be understood however that any suitable oxidation systems which selectively oxidizes the C-16 hydroxyl group can be used in practicing this invention.

The oxidation reaction is generally conducted at a temperature ranging between about 25° C. and about 100° C., preferably about 25° C., for a period ranging between about 12 and about 24 hours, preferably about 24 hours.

Thereafter, the excess oxidizing agent in the reaction mixture is quenched by the addition of an alcohol, e.g. methanol, and the product, (25R)-16-oxo-26-phthalimidocholesterol (5), is extracted from the mixture with an appropriate solvent, e.g. methylene chloride, and purified by conventional means such as thin layer or column chromatography and recrystallization. A preferred method of purification is recrystallization from acetone.

(25R)-16-Oxo-26-phthalimidocholesterol (5) is then subjected to a modified Wolff-Kishner reduction which simultaneously reduces the C-16 oxo moiety and cleaves the phthalimide group to form (25R)-26-aminocholesterol (1).

The reduction reaction mixture contains (25R)-16--oxo-26-phthalimidocholesterol (5), hydrazine monohydrate, and potassium hydroxide in polyethylene glycol solvent in a molar ratio of between about 1:60:14 and about 1:75:16, preferably about 1:66:15. The amount of polyethylene glycol used generally ranges between about 30 ml and about 40 ml per gram of steroid, preferably about 35 ml.

The reaction mixture is heated to a constant temperature ranging between about 195° C. and about 215° C., preferably about 200° C., and refluxed at this temperature until water distills off. Thereafter, the reaction is maintained at this temperature for a period of between about 1 hour and about 3 hours, preferably about 2 hours, then cooled to room temperature. The reaction mixture is then poured into water and the product, (25R)-26-aminocholesterol (1) is extracted with an appropriate solvent, e.g. chloroform, and purified by conventional means which includes thin layer or column chromatography and recrystallization. A preferred method of purification is recrystallization from methylene chloride-ether mixtures.

An alternative procedure for preparing (25R)-16-oxo-26-phthalimidocholesterol (5) is also illustrated in Scheme 1. According to Scheme 1, (25R)-16,26-dihydroxycholesterol-3β,26-ditosylate (6) is prepared from intermediate (2). In preparing intermediate (6), the amount of toluenesulfonyl chloride is generally ranges between about 2 and about 4 mole equivalents, preferably at least 2 mole equivalents per mole of intermediate (2). The conditions for the tosylation are the same as described above.

Thereafter, (25R)-16,26-dihydroxycholesterol-3β,26-ditosylate (6) is then subjected to chemical oxidation at the C-16 position to form (25R)-16-dihydroxycholesterol-3β,26-ditosylate (7). Any suitable oxidation system can be employed to effect this conversion which is selective for the C-16 hydroxyl group. A preferred oxidation agent for use in preparing intermediate (7) is Jone's reagent. The conditions for the chemical oxidation are the same as described above.

(25R)-16-Oxo-26-hydroxycholesterol-3β,26-ditosylate (7) is subjected to solvolytic conditions which results in the selective hydrolysis of the C-3 tosylate to form (25R)-16-oxo-26-hydroxycholesterol-26-tosylate (8). In general, the solvolysis is effected with aqueous acidic solutions containing an organic solvent and a catalytic amount of acid. Suitable temperatures for effecting the solvolysis range between about 20° C. and about 100° C., preferably between about 25° C. and about 60° C. An appropriate choice of temperature is dependent on the choice of the solvent system and is one that results in short reaction times (less than about 24 hours) but insufficient to cause undesirable elimination or degradation reactions of intermediate (8).

Suitable, but non-limiting, acid catalysts for effecting solvolysis include sulfuric acid, hydrochloric acid and pyridinium p-toluenesulfonate (PPTs). A preferred acid for use in practicing the invention is sulfuric acid. The amount of acid that can be used ranges between about 10 microliters and about 1 ml per 100 ml of solvent. It will be understood that the amount of acid used is insufficient to cause undesirable elimination or degradation reactions of the intermediate.

Non-limiting examples of suitable solvents include acetone, dioxane, tetrahydrofuran, alcohols, e.g methanol, and mixtures thereof. A preferred solvent for use in the reaction is acetone. The amount of solvent that can be employed is an amount sufficient to at least dissolve the steroid under reaction conditions.

(25R)-16-oxo-26-hydroxycholesterol-26-tosylate (8) is then reacted with a phthalimide salt to form (25R)-16-oxo-26-phthalimidocholesterol (5). Suitable phthalimide salts, displacement reaction conditions and methods for purification are the same as described above.

Scheme 2 illustrates another embodiment of the present invention. According to this scheme, (25R)-16$\beta$,26-dihydroxycholesterol (2) is initially subjected to oxidizing conditions which results in the selective oxidation of the C-16 alcohol to form (25R)-16-oxo-26-hydroxycholesterol (9). A number procedures have been reported in the literature for preparing this intermediate and its derivatives. See, for example, Tschesche et al. (1979); Arunachalam et al. (1981); and Seo et al. (1986) as well as references cited therein.

Thereafter, (25R)-16-oxo-26-hydroxycholesterol (9) is converted to (25R)-16-oxo-26-hydroxycholesterol-26-tosylate (8) directly or indirectly by solvolysis of a (25R)-16-oxo-26-hydroxycholesterol-3$\beta$,26--ditosylate (7). Intermediate (8) is then subjected to displacement reaction with a phthalimide salt to form (25R)-16-oxo-26-phthalimidocholesterol (5). The reaction conditions and reagents for effecting all these conversions are the same as described above.

The following examples are illustrative and do not serve to limit the scope of the invention as claimed.

EXAMPLE 1: PREPARATION OF (25R)-16$\beta$,26-DIHYDROXYCHOLESTEROL (2)

To a 5-liter flask were sequentially added diosgenin (40 grams, 0.0965 moles, zinc dust (900 grams, −325 mesh size) and 2 liters of absolute ethanol. The suspension was then brought to reflux and 800 ml of concentrated HCl was added dropwise over a period of 2.5 hours. The reaction was refluxed for an additional 30 minutes then immediately filtered while hot, under gravity, over Whatman no. 2 filter paper to remove the zinc particles. Two liters of water was then added to the filtrate and a white precipitate formed. The mixture was cooled at room temperature and the precipitate was collected by suction filtration (Whatman no. 2 paper) and washed three times with water, then air dried to afford 35 grams (85% yield) of compound (2).

EXAMPLE 2: PREPARATION OF (25R)-16$\beta$,26-DIHYDROXYCHOLESTEROL 26-TOSYLATE (3)

To a solution containing (25R)-16$\beta$, 26-dihydroxycholesterol (2) (0.35 g, 0.84 mmoles in 10 ml pyridine), cooled in a ice bath, p-toluenesulfonyl chloride (0.44 g, 2.31 mmoles) was added and stirred for 15 hours at 0° C. The reaction mixture was then poured into water and extracted with ether. The organic layer was washed with 2N HCl and water, dried over sodium sulfate, and evaporated under reduced pressure. Chromatography of the residue on silica gel eluted with CHCl$_3$/n-Hexanes(3:1) gave 0.29 g (61%) of (25R)-16$\beta$, 26-dihydroxycholesterol 26-tosylate (3). The product was crystallized from methanol-water and found to have a melting point of 55° C. Elemental and structural ($^1$H-NMR) analyses of the product are described below.

| Elemental Analysis (Formula C$_{34}$H$_{52}$O$_5$ S) | | |
|---|---|---|
| | C (%) | H (%) |
| Calc. | 71.29 | 9.15 |
| Found | 71.56 | 9.14 |
| NMR (ppm, CDCl$_3$) | | |
| 2.43(3H, s, aryl-CH$_3$); 3.3–3.7(1H, m, 3$\alpha$-H); | | |
| 3.83(2H, brd, 26-CH$_2$, J=6Hz); 4.1–4.5(1H, m, 16$\alpha$-H); | | |
| 5.3–5.5(1H, m, 6-H); 7.29(2H, d, aryl-H, J=8Hz); | | |
| 7.73(2H, d, aryl-H, J=8Hz) | | |

EXAMPLE 3: PREPARATION OF (25R)-16$\beta$, 26-DIHYDROXYCHOLESTEROL 26-TOSYLATE (3)

In this Example, intermediate (3) was prepared from (25R)-16$\beta$, 26-dihydroxycholesterol (2) under similar reaction conditions as described in Example 2, except the reaction was conducted at room temperature.

To a solution of (25R)-16$\beta$, 26-dihydroxycholesterol (2) (0.30 g, 0.72 mmoles in 10 ml pyridine), cooled in an ice bath, p-toluenesulfonyl chloride (0.83 g, 4.35 mmoles) was added and the mixture was stirred for 5 hours at room temperature. Afterwards, the mixture was poured into water and extracted with ether. The organic layer was washed with 2N HCl and water, and evaporated under reduced pressure. Acetone (50 ml), water (20 ml) and a catalytic amount of sulfuric acid (0.2 ml) was added to the residue and the mixture was refluxed for 6 hours. The acetone was evaporated and the resulting precipitate was filtered out. Chromatography of the precipitate on silica gel eluted with CHCl$_3$ gave 0.37 g (90%) of the product which is the same as the one found in Example 2. The compound was crystallized from methanol-water and was found to have a melting point of 55° C.

EXAMPLE 4: PREPARATION OF (25R)-16$\beta$-HYDROXY-26-PHTHALIMIDO-CHOLESTEROL (4)

A reaction mixture of (25R)-16$\beta$, 26-dihydroxycholesterol 26-tosylate (3) (0.21 g, 0.37 mmoles), potassium phthalimide (0.21 g, 1.13 mmoles), and DMF (16 ml) was stirred for four days at room temperature. The reaction mixture was then poured into water, and extracted twice with methylene chloride. The pooled extracts were washed with 2N Hcl and water, dried over sodium sulfate and evaporated under reduced pressure to yield 0.18 g (90%) of (25R)-16$\beta$-hydroxy-26-phthalimidocholesterol (4). The product was recrystallized from ethyl acetate and was found to have a melting point of 134.5°–136° C.

| Elemental Analysis (Formula $C_{35}H_{49}NO_4$) | | | |
|---|---|---|---|
| | C (%) | H (%) | N (%) |
| Calc. | 76.74 | 9.02 | 2.56 |
| Found | 76.61 | 9.09 | 2.40 |
| NMR (ppm, CDCl$_3$) | | | |
| 3.2–3.8(3H, m, 3α-H, 26-CH$_2$); 4.1–4.5(1H, m, 16α-H); | | | |
| 5.2–5.4(1H, m, 6-H); 7.5–7.9(4H, m, aryl-H) | | | |

EXAMPLE 5: PREPARATION OF (25R)-16β-HYDROXY-26-PHTHALIMIDO-CHOLESTEROL (4)

In this Example, intermediate (4) was prepared from (25R)-16β, 26-dihydroxycholesterol 26-tosylate (3) under similar reaction conditions as described in Example 4, except the reaction was conducted at 100° C.

A reaction mixture of (25R)-16β, 26-dihydroxycholesterol 26-tosylate (3) (0.20 g, 0.35 mmoles), potassium phthalimide (0.20 g, 1.08 mmoles) and DMF (10 ml) was stirred for 1.5 hours at 100° C. Thereafter, the reaction mixture was poured into water and extracted with methylene chloride. The extract was washed with 2N HCl and water, dried over sodium sulfate and evaporated under reduced pressure to yield 0.18 g (94%) of the product which is the same as the one produced in Example 4. The compound was recrystallized from ethyl acetate and was found to have a melting point of 134.5°–136° C.

EXAMPLE 6: PREPARATION OF (25R)-16β, 26-DIHYDROXYCHOLESTEROL 3β, 26-DITOSYLATE (6)

To a solution of (25R)-16β, 26-dihydroxycholesterol (2) (1.89 g, 4.52 mmoles in pyridine (20 ml)), cooled in an ice bath, p-toluenesulfonyl chloride (3.44 g, 18.0 mmoles) was added and the mixture stirred for 5 hours at room temperature. The reaction mixture was then poured into water and extracted with ether. The organic layer was washed with 2N HCl and water, dried over sodium sulfate, and evaporated under reduced pressure to yield 3.04 g (93%) of (25R)-16β, 26-dihydroxycholesterol 3β, 26-ditosylate as an oil. Structural analyses of the product by IR and $^1$H-NMR are described below.

IR (KBr)
3550,2930,2850,1600,1360,1190,1180,1100,940,670,5-60
cm$^{-1}$
NMR (ppm, CDCl$_3$)
2.43(6H,s,aryl—CH$_3$);3.83(2H,br—d,-26—CH$_2$,J=6Hz);
4.0–4.6(1H,m,3α-H,16αH);5.1–5.4(1H,m,6-H);
7.28(2H,d,aryl-H,J=8Hz); 7.75(2H,d,aryl-H,J=8Hz)

EXAMPLE 7: PREPARATION OF (25R)-26-HYDROXY-16-OXOCHOLESTEROL 3β, 26-DITOSYLATE (7) FROM INTERMEDIATE (6)

Jone's reagent was added dropwise to a solution of (25R)-16β, 26-dihydroxycholesterol 3β, 26-ditosylate (6) (3.04 g, 5.41 mmoles) in acetone (70 ml) at room temperature until a brown-orange color persisted, followed by stirring for an additional 10 minutes. The reaction mixture was quenched with saturated NaHSO$_3$ aqueous solution, then diluted with water, and extracted with ether. The organic layer was washed with water, dried over sodium sulfate, and evaporated under reduced pressure to yield 2.85 g (94%) of (25R)-26-hydroxy-16-oxocholesterol 3β, 26-ditosylate (7) as an oil. Structural analyses of the product by IR and $^1$H-NMR are described below.

IR (KBr)
3450,2930,2850,1730,1600,1360,1190,1180,1100,930,6-60,
560 cm$^{-1}$
NMR (ppm, CDCl$_3$)
2.43(6H,s,aryl—CH$_3$);3.83(2H,br—d,-26—CH$_2$,J=6Hz);
4.0–4.6(1H,m,3α-H);5.1–5.4(1H,m,6-H);
7.28(2H,d,aryl-H,J=8Hz);7.75(2H,d,aryl-H,J=8Hz)

EXAMPLE 8: PREPARATION OF (25R)-26-HYDROXY-16-OXOCHOLESTEROL 26-TOSYLATE (8)

A mixture of (25R)-26-hydroxy-16-oxocholesterol 3β, 26-ditosylate (7) (2.00 g, 2.76 mmoles), acetone (60 ml), water (25 ml) and a catalytic amount of sulfuric acid was refluxed for 6 hours. Acetone was removed from the mixture which was then diluted with water and extracted with ether. The organic layer was washed with water, dried over sodium sulfate, and evaporated under reduced pressure to yield 1.51 g (96%) of (25R)-26-hydroxy-16-oxocholesterol 26-tosylate (8). The product was recrystallized from carbon tetrachloride and was found to have a melting point of 114°–115° C. Elemental and structural $^1$H-NMR) analyses of the product are described below.

| Elemental Analysis (Formula $C_{34}H_{50}O_5S$) | | |
|---|---|---|
| | C (%) | H (%) |
| Calc. | 71.54 | 8.83 |
| Found | 71.15 | 8.75 |
| NMR (ppm, CDCl$_3$) | | |
| 2.43(3H, s, aryl-CH$_3$); 3.3–3.7(1H, m, 3α-H); | | |
| 3.83(2H, br-d, 26-CH$_2$, J=6Hz); 5.2–5.5(1H, m, 6-H); | | |
| 7.28(2H, d, aryl-H. J=8Hz); 7.73(2H, d, aryl-H, J=8Hz) | | |

EXAMPLE 9: PREPARATION OF (25R)-16-OXO-26-PHTHALIMIDOCHOLESTEROL (5) FROM INTERMEDIATE (4)

A solution of chromium trioxide (0.04 g, 0.4 mmoles) in water (0.15 ml) and acetic acid (0.3 ml) was added dropwise to a solution of (25R)-16β-hydroxy-26-phthalimidocholesterol (4) (0.26 g, 0.49 mmoles), and sodium acetate (1.00 g, 12.19 mmoles) in acetic acid (35 ml), and stirred for 18 hours at room temperature. The excess reagent was then destroyed with methanol (15 ml), and solvent was evaporated under reduced pressure. The resulting residue was diluted with water, and extracted with methylene chloride. The organic layer was washed with 5% K$_2$CO$_3$ and water, dried over sodium sulfate, and evaporated under reduced pressure to yield 0.23 g (89%) of (25R)-16-oxo-26-phthalimidocholesterol (5). The product was recrystallized from acetone and was found to have a melting point of 178°–180° C. Elemental and structural $^1$H-NMR) analyses of the product are described below.

| Elemental Analysis (Formula $C_{35}H_{47}NO_4$) | | | |
|---|---|---|---|
| | C (%) | H (%) | N (%) |
| Calc. | 77.03 | 8.68 | 2.57 |
| Found | 76.83 | 8.71 | 2.40 |

-continued

| Elemental Analysis (Formula $C_{35}H_{47}NO_4$) | | |
|---|---|---|
| C (%) | H (%) | N (%) |

NMR (ppm, CDCl$_3$)
3.4–3.8(3H, m, 3α-H, 26-CH$_2$); 5.2–5.5(1H, m, 6-H);
7.5–8.0(4H, m, aryl-H)

NMR (ppm, CDCl$_3$)
3.4–3.8(3H,m,3α-H,26—CH$_2$);5.2–5.5(1H,m,6-H);
7.5–8.0(4H,m,aryl-H)

EXAMPLE 10: PREPARATION OF (25R)-16-OXO-26-PHTHALIMIDOCHOLESTEROL (5) FROM INTERMEDIATE (8)

A mixture of (25R)-26-hydroxy-16-oxocholesterol 26-tosylate (8) (0.96 g, 1.71 mmoles), potassium phthalimide (0.62 g, 3.35 mmoles), and DMF (7 ml) was stirred for 2 hours at 100° C. The reaction mixture was then poured into water and extracted with ethyl acetate. The extract was washed twice with 2N-HCl and water, dried over sodium sulfate, and evaporated under reduced pressure to yield 0.84 (92%) of the product which is the same as the one produced in Example 9. The compound was recrystallized from acetone and was found to have a melting point of 178°–180° C.

EXAMPLE 11: PREPARATION OF (25R)-16-OXO-26-HYDROXYCHOLESTEROL (9)

A solution of chromium trioxide (80 mg) in water (0.4 ml) and acetic acid (0.8 ml) is added dropwise to a solution of (25R)-16β,26-dihydroxycholesterol (2) (0.500 g), and sodium acetate (2.48 g) in glacial acetic acid (90 ml), and is stirred for 18 hours at room temperature. The excess reagent is then destroyed with methanol (15 ml), and solvent is evaporated under reduced pressure. The resulting residue is diluted with water, and extracted with methylene chloride. The organic layer is washed with 5% K$_2$CO$_3$ and water, dried over sodium sulfate, and evaporated under reduced pressure to yield 0.48 g of crude product. The mixture is resolved by silica flash column chromatography (hexanes:ethyl acetate) to afford 0.313 g of (25R)-16-oxo-26-hydroxycholesterol (9). M.pt. 167°–169° C.

EXAMPLE 12: PREPARATION OF (25R)-26-HYDROXY-16-OXOCHOLESTEROL 3β, 26-DITOSYLATE (7) FROM INTERMEDIATE (9)

To a solution of (25R)-26-hydroxy-16-oxocholesterol (9) (4.52 mmoles in pyridine (20 ml)), cooled in an ice bath, p-toluenesulfonyl chloride (3.44 g, 18.0 mmoles) is added mixture is stirred for 5 hours at room temperature. The reaction mixture is then poured into water and extracted with ether. The organic layer is washed with 2N HCl and water, dried over sodium sulfate, and evaporated under reduced pressure to yield 3.04 g (93%) of (25R)-16β, 26-dihydroxycholesterol 3β, 26-ditosylate (7) as an oil. The product is the same as the one in Example 8.

EXAMPLE 13: PREPARATION OF (25R)-26-HYDROXY-16-OXOCHOLESTEROL 26-TOSYLATE (8) FROM INTERMEDIATE (9)

To a solution containing (25R)-26-hydroxy-16-oxocholesterol (9) (0.84 mmoles in 10 ml pyridine), cooled in a ice bath, p-toluenesulfonyl chloride (0.44 g, 2.31 mmoles) is added and stirred for 15 hours at 0° C. The reaction mixture is then poured into water and extracted with ether. The organic layer is washed with 2N HCl and water, dried over sodium sulfate, and evaporated under reduced pressure. Chromatography of the residue on silica gel eluted with CHCl$_3$/n-Hexanes(3:1) gave 0.29 g (61%) of (25R)-26-hydroxy-16-oxocholesterol 26-tosylate (8) which is the same as the product in Example 8. The product is crystallized from methanol-water and is found to have a melting point of 55° C.

EXAMPLE 14: PREPARATION OF (25R)-26-AMINOCHOLESTEROL (1)

A mixture of (25R)-16-oxo-26-phthalimidocholesterol (5) (0.70 g, 1.32 mmoles), hydrazine monohydrate (5 ml, 102.8 mmoles), potassium hydroxide (2.85 g, 50.8 mmoles) and triethylene glycol (20 ml) was heated to 150° C. for 30 minutes, then heated to 200° C. over 2 hours during which time water vapor distilled out of the mixture. The reaction mixture was maintained at this temperature for about 16 hours, under nitrogen, until the reaction was complete as determined by thin layer chromatography. Thereafter, the reaction mixture was cooled, poured into water, and extracted with chloroform. The extract was washed with water, dried over sodium sulfate, and evaporated under reduced pressure. Chromatography of the residue on silica gel eluted with CHCl$_3$ gave 0.34 g (66%) of (25R)-26-aminocholesterol. The product was recrystallized from methylene chloride-ether and was found to have a melting point of 150°–152° C.

| Elemental Analysis (Formula $C_{27}H_{47}NO$) | | |
|---|---|---|
| | C (%) | H (%) | N (%) |
| Calc. | 80.74 | 11.79 | 3.49 |
| Found | 80.49 | 11.97 | 3.31 |

What is claimed is:

1. A method for preparing (25R)-26-aminocholesterol which comprises reducing (25R)-16-oxo-26-phthalimidocholesterol.

2. The method according to claim 1 which comprises effecting the reduction with hydrazine in the presence of an alkali salt.

3. The method according to claim 1 further comprising prior to said reduction,
    reacting (25R)-16β, 26-dihydroxycholesterol 26-tosylate with a phthalimide salt to form (25R)-16β-hydroxy-26-phthalimidocholesterol; and
    oxidizing (25R)-16β-hydroxy-26-phthalimidocholesterol to form (25R)-16-oxo-26-phthalimidocholesterol.

4. The method according to claim 3 which comprises effecting the oxidation with chromium trioxide in acetic acid.

5. The method according to claim 1 further comprising prior to said reduction,
    condensing (25R)-16β, 26-dihydroxycholesterol with p-toluenesulfonyl chloride to form (25R)-16β, 26-dihydroxycholesterol 3β, 26-ditosylate;
    oxidizing (25R)-16β, 26-dihydroxycholesterol 3β, 26-ditosylate to form (25R)-26-hydroxy-16-oxocholesterol 3β, 26-ditosylate;
    hydrolyzing (25R)-26-hydroxy-16-oxocholesterol 3β, 26-ditosylate to form (25R)-26-hydroxy-16-oxocholesterol 26-tosylate; and
    reacting (25R)-26-hydroxy-16 -oxocholesterol 26-tosylate with a phthalimide salt to form (25R)-16-oxo-26-phthalimidocholesterol.

6. The method according to claim 5 which comprises effecting the oxidation with chromium trioxide in acetic acid.

7. The method according to claim 5 which comprises hydrolyzing with an aqueous acid solution.

8. The method according to claim 1 further comprising prior to said reduction,
   oxidizing (25R)-16β,26-dihydroxycholesterol to form (25R)-16-oxo-26-hydroxycholesterol;
   condensing (25R)-16-oxo-26-hydroxycholesterol with p-toluenesulfonyl chloride to form (25R)-16-oxo-26-hydroxycholesterol-26-tosylate; and
   reacting (25R)-16-oxo-26-hydroxycholesterol-26-tosylate with a phthalimide salt to form (25R-16-oxo-26-phthalimidocholesterol.

9. The method according to claim 1 further comprising prior to said reduction,
   oxidizing (25R)-16β,26-dihydroxycholesterol to form (25R)-16-oxo-26-hydroxycholesterol;
   condensing (25R)-16-oxo-26-hydroxycholesterol with p-toluenesulfonyl chloride to form (25R)-16-oxo-26-hydroxycholesterol-3,26-ditosylate;
   hydrolyzing (25R)-16-oxo-26-hydroxycholesterol-3,26-ditosylate to form (25R)-16-oxo-26-hydroxycholesterol-26-tosylate; and
   reacting (25R)-16-oxo-26-hydroxycholesterol-26-tosylate with a phthalimide salt to form (25R-16-oxo-26-phthalimidocholesterol.

10. (25R)-16-oxo-26-phthalimidocholesterol.

* * * * *